US012698533B2

(12) United States Patent
Lee et al.

(10) Patent No.: US 12,698,533 B2
(45) Date of Patent: Aug. 4, 2026

(54) COMPOSITION FOR DIAGNOSIS OR PREDICTION OF METABOLIC SYNDROME OR GROUP AT HIGH RISK OF EXPRESSION OF BLOOD CERAMIDE

(71) Applicant: SCL HEALTHCARE, CO., LTD., Yongin-si (KR)

(72) Inventors: Sang Hoo Lee, Yongin-si (KR); Ye Jin Kim, Yongin-si (KR); Ju Hoon Kim, Yongin-si (KR); Jeong Hoon Hong, Yongin-si (KR); Yi Seul Kim, Yongin-si (KR); Sae Yun Baik, Yongin-si (KR); Kyoung Ryul Lee, Yongin-si (KR)

(73) Assignee: SCL HEALTHCARE, CO., LTD., Yongin-si (KR)

( * ) Notice: Subject to any disclaimer, the term of this patent is extended or adjusted under 35 U.S.C. 154(b) by 653 days.

(21) Appl. No.: 18/248,133

(22) PCT Filed: Sep. 16, 2021

(86) PCT No.: PCT/KR2021/012700
§ 371 (c)(1),
(2) Date: Apr. 6, 2023

(87) PCT Pub. No.: WO2022/075627
PCT Pub. Date: Apr. 14, 2022

(65) Prior Publication Data
US 2024/0011097 A1 Jan. 11, 2024

(30) Foreign Application Priority Data
Oct. 6, 2020 (KR) ........................ 10-2020-0128464

(51) Int. Cl.
*C12Q 1/6883* (2018.01)

(52) U.S. Cl.
CPC ..... *C12Q 1/6883* (2013.01); *C12Q 2600/156* (2013.01)

(58) Field of Classification Search
None
See application file for complete search history.

(56) References Cited

U.S. PATENT DOCUMENTS

2006/0211020 A1* 9/2006 Farrer .................. C12Q 1/6883
514/4.8
2013/0338027 A1* 12/2013 Muraca .............. G01N 33/6893
435/7.1
2019/0264262 A1 8/2019 Ko et al.

FOREIGN PATENT DOCUMENTS

| CN | 105296619 A | 2/2016 | |
| KR | 1020080067929 A | 7/2008 | |
| KR | 101815692 B1 | 1/2018 | |
| KR | 1020190043449 A | 4/2019 | |
| KR | 101979633 B1 | 5/2019 | |
| KR | 1020190115836 A | 10/2019 | |
| KR | 102039529 B1 * | 11/2019 | ......... G01N 33/6893 |
| KR | 102115933 B1 | 5/2020 | |
| WO | 2009150550 A2 | 12/2009 | |

OTHER PUBLICATIONS

Good et al. Twin Research and Human Genetics. 2019. 22: 79-87 (Year: 2019).*
Cohen et al Shock. Mar. 2020. 53(3): 256-268 (Year: 2020).*
ISA/KR "International Search Report for PCT Application No. PCT/KR2021/012700" issued by the Korean Intellectual Property Office, Korea, Dec. 23, 2021.
"The role of C16:0 ceramide in the development of obesity and type 2 diabetes: CerS6 inhibition as a novel therapeutic approach", Suryaprakash Raichur et al., Molecular Metabolism 21, 2019, pp. 36-50.
Notice of Allowance issued by the Korean Intellectual Property Office for Application No. 10-2020-0128464, Korea, Nov. 17, 2020.
Joe Erin et al., Study on the main types of metabolic syndrome and their relationship with SNPs, Dec. 2004.
Timothy Hla et al., C16:0-Ceramide Signals Insulin Resistance, Cell Metabolism 20, Nov. 4, 2014, pp. 703-705.
Li Ying et al., Cermaide Dependent Lipotoxicity in Metabolic Diseases, Nutrition and Healthy Aging, 2019, 5, pp. 1-12.
Maria Kolak et al., Expression of ceramide-metabolising enzymes in subcutaneous and intra-abdominal human adipose tissue, Lipids in Health and Disease, 2012, 11:115, pp. 1-12.
Marta Sarkozy et al., Transcriptomic alterations in the heart of non-obese type 2 diabetic Goto-Kakizaki rats, Cardiovascular Diabetology, 2016, 15:110, pp. 1-21.

* cited by examiner

*Primary Examiner* — Carla J Myers
(74) *Attorney, Agent, or Firm* — Troutman Pepper Locke LLP; Tim Tingkang Xia, Esq.

(57) ABSTRACT

The present invention relates to a composition for diagnosing or predicting a metabolic syndrome and a composition for predicting a group at high risk of expression of blood ceramide and to a single nucleotide polymorphism (SNP), derived through a genome wide association study (GWAS), capable of predicting metabolic syndrome and a group at high risk of expression of blood ceramide, which is a risk factor for metabolic syndrome. When used, a SNP marker derived by the present invention makes it possible to diagnose or predict metabolic syndrome and to predict a group at high risk of expression of blood ceramide, whereby patients suffering from the metabolic syndrome caused by a high expression of blood ceramide can be effectively diagnosed and managed. On the basis of these effects, the present invention can find wide applications in the pharmaceutical industry, etc.

5 Claims, 1 Drawing Sheet
Specification includes a Sequence Listing.

| ceramide / functional term | C16_ Dihydroceramide | C18_ Dihydroceramide | C24_ Dihydroceramide | C24:1_ Dihydroceramide | C16_Ceramide | C18_Ceramide | C20_Ceramide | SNP Name |
|---|---|---|---|---|---|---|---|---|
| CERS4 (Ceramide Synthase 4) | 0.9773 | 0.3973 | 0.4966 | 0.9701 | 0.1464 | 0.9328 | 0.5018 | |
| CERS6 (Ceramide Synthase 6) | 0.7519 | 0.6420 | 0.6773 | 0.5365 | | 0.1419 | | rs7597925 |
| CERS3 (Ceramide Synthase 3) | 0.864 | 0.3555 | 0.7096 | 0.5283 | | 0.6756 | 0.9418 | rs72759182 |
| CERS3 (Ceramide Synthase 3) | 0.8317 | 0.4292 | 0.9618 | 0.6505 | | 0.9856 | 0.5502 | rs4246316 |
| CERS3 (Ceramide Synthase 3) | 0.5586 | 0.1574 | 0.1027 | 0.3039 | 0.9742 | 0.5316 | 0.7081 | |
| CERS4 (Ceramide Synthase 6) | 0.7434 | 0.7747 | 0.286 | 0.3863 | 0.11 | 0.3399 | 0.1284 | |
| CERS6 (Ceramide Synthase 6) | 0.2326 | 0.7478 | 0.6984 | 0.396 | | 0.3393 | 0.1363 | rs80165332 |
| CERS6 (Ceramide Synthase 6) | 0.06967 | 0.7783 | 0.3783 | 0.5331 | 0.4304 | 0.2954 | 0.1118 | |
| ACER1 (Alkaline Ceramidase 1) | 0.2025 | 0.5532 | 0.4684 | 0.7137 | 0.4533 | 0.4813 | 0.4044 | |
| ACER1 (Alkaline Ceramidase 1) | 0.0923 | | | | 0.1404 | 0.02405 | 0.05666 | rs42106818 |
| SGMS1 (Sphingomyelin Synthase 1) | 0.7911 | 0.3767 | 0.20 | 0.3491 | | | | rs12258093 |
| SGMS1 (Sphingomyelin Synthase 1) | 0.2792 | 0.1476 | | 0.05112 | | | | rs11006229 |
| SGMS1 (Sphingomyelin Synthase 1) | 0.9707 | 0.7593 | 0.8424 | 0.4196 | 0.2765 | 0.9917 | 0.3515 | |
| SGMS1 (Sphingomyelin Synthase 1) | 0.4618 | 0.1484 | 0.3 | 0.4342 | 0.1269 | | 0.08073 | rs10828074 |
| SPTLC2 (Serine Palmitoyltransferase Long Chain Base Subunit 2) | 0.5394 | 0.4519 | 0.4659 | 0.4835 | 0.07722 | 0.1096 | | rs149162405 |
| SPTLC3 (Serine Palmitoyltransferase Long Chain Base Subunit 3) | 0.516 | 0.7992 | 0.8647 | 0.5891 | 0.2081 | 0.275 | 0.3375 | |
| SPTLC3 (Serine Palmitoyltransferase Long Chain Base Subunit 3) | 0.06409 | 0.1728 | 0.2556 | 0.343 | | 0.5792 | 0.4299 | rs6109681 |
| SPTLC3 (Serine Palmitoyltransferase Long Chain Base Subunit 3) | 0.7307 | 0.4860 | 0.7805 | 0.7706 | | 0.394 | 0.1911 | rs9806631 |
| SPTLC3 (Serine Palmitoyltransferase Long Chain Base Subunit 3) | 0.7001 | 0.7299 | 0.9148 | 0.6693 | 0.05182 | 0.1591 | 0.1216 | |
| SGPP2 (Sphingosine-1-Phosphate Phosphatase 2) | 0.3066 | 0.9585 | 0.7187 | 0.8925 | 0.08915 | 0.3354 | 0.1942 | |
| UGCG (UDP-Glucose Ceramide Glucosyltransferase) | | 0.08021 | 0.3021 | 0.1063 | | 0.2725 | 0.4116 | rs1213202 |

COMPOSITION FOR DIAGNOSIS OR PREDICTION OF METABOLIC SYNDROME OR GROUP AT HIGH RISK OF EXPRESSION OF BLOOD CERAMIDE

SEQUENCE LISTING

This application includes a Sequence Listing in the ASCII text file in .txt format in accordance with 37 C.F.R. § 1.821, electronically submitted via the USPTO patent electronic filing system on Jul. 13, 2023. The ASCII text file contains a sequence listing entitled "1009082.105US9_Sequence-Listing_ST.25.txt" created on Apr. 4, 2023 and is 4,834 bytes in size. The Sequence Listing contained in this 10090$2.105US91009082.105US9_Sequence-Listing_ST.25.txt file is part of the specification and is hereby incorporated by reference herein in its entirety.

TECHNICAL FIELD OF THE INVENTION

The present invention relates to a composition for diagnosing or predicting metabolic syndrome and a composition for predicting a group at high risk of expression of blood ceramide, and to a single nucleotide polymorphism (SNP), derived through a genome wide association study (GWAS), and capable of predicting metabolic syndrome and a group at high risk of expression of blood ceramide, which is a risk factor for metabolic syndrome.

BACKGROUND OF THE INVENTION

Since metabolic syndrome was named by Reaven GM in 1988, the metabolic syndrome has become a common health problem in primary care. The prevalence of the metabolic syndrome in the primary care is known to reach about 30%, and the higher the age and the higher the degree of obesity are, the higher the prevalence. The medical importance of the metabolic syndrome is revealed from the fact that the mortality rate of cardiovascular diseases is higher in the presence of the metabolic syndrome than in the absence of the metabolic syndrome. Even in Korea, since the obese population is gradually increasing and the prevalence of cardiovascular diseases such as hypertension, diabetes, and hyperlipidemia is rapidly increasing, recently, efforts to manage metabolic indicators of the body prior to the onset of metabolic syndrome have been continued in consideration of the fact that mortality due to cardiovascular disease is the second highest in men and women. However, even if there are no symptoms or only one risk factor is present, the metabolic syndrome is highly likely to develop chronic diseases such as hypertension, diabetes, hyperlipidemia, and obesity due to complex interactions with each other, and thus, it is required to manage complex metabolism-related factors, but it is not properly performed.

Type 2 diabetes and metabolic syndrome, which show an explosive increase in recent years, show a close correlation with the increase in the obese population and are characterized by insulin resistance. Triglycerides, which account for most of the fat accumulated in the muscle and liver, are in a chemically inactive form. In addition, when diacylglycerol acyltransferase 1 (DGAT1), a final step in triglyceride synthesis, is overexpressed in the muscle and liver, triglycerides are increased, but there is no correlation with insulin resistance. Thus, it is considered that lipid metabolites, which act as physiologically active substances rather than triglycerides accounting for most of the accumulated fat, are involved in occurrence of insulin resistance by inhibiting an insulin signaling system. These lipid metabolites include long-chain acyl CoA of a triglyceride pathway, lysophosphatidic acid, phosphatidic acid, diacylglycerol (DAG), sphingolipid-based ceramides, and the like.

Meanwhile, a single nucleotide polymorphism of an individual gene refers to a genetic change or mutation showing a difference in one nucleotide sequence (A, T, G, C) in a DNA sequence, and since the single nucleotide polymorphism is a part that shows a lot of mutations in each individual, the single nucleotide polymorphism is mainly used for DNA fingerprinting analysis. Since it is possible to consider differences in basic metabolic abilities inherent in individual genes by using single nucleotide polymorphism analysis, it is possible to manage complex metabolic syndrome more effectively.

Therefore, based on the association between metabolic syndrome and blood ceramide, there is an urgent need to identify clinically useful SNP markers for predicting metabolic syndrome or a group at high risk of expression of blood ceramide.

Technical Problem

The present inventors selected SNPs associated with metabolic syndrome by comparing a patient group with metabolic syndrome with a normal control through a genome wide association study (GWAS), compared and analyzed an association between the selected SNPs and a blood ceramide level again to finally derive an SNP with a significant association, and then completed the present invention.

Accordingly, an object of the present invention is to provide a marker composition for predicting or diagnosing metabolic syndrome, including an SNP associated with the metabolic syndrome and a blood ceramide concentration.

Another object of the present invention is to provide a marker composition for predicting a group at high risk of expression of blood ceramide, including an SNP associated with the metabolic syndrome and a blood ceramide concentration.

Yet another object of the present invention is to provide a method for diagnosing and treating metabolic syndrome using an SNP associated with the metabolic syndrome and a blood ceramide concentration.

Technical Solution

One aspect of the present invention provides a marker composition for predicting or diagnosing metabolic syndrome including: a polynucleotide consisting of 10 to 100 consecutive DNA sequences including a single nucleotide polymorphism in which a base at position 101 is C or G in a polynucleotide represented by SEQ ID NO: 1; or a polynucleotide consisting of 10 to 100 consecutive DNA sequences including a single nucleotide polymorphism in which a base at position 101 is C or T in a polynucleotide represented by SEQ ID NO: 2.

Another aspect of the present invention provides a composition for predicting or diagnosing metabolic syndrome including a preparation capable of detecting a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

Yet another aspect of the present invention provides a marker composition for predicting a group at high risk of expression of blood ceramide including: a polynucleotide consisting of 10 to 100 consecutive DNA sequences including a single nucleotide polymorphism in which a base at position 101 is C or G in a polynucleotide represented by SEQ ID NO: 1; or a polynucleotide consisting of 10 to 100 consecutive DNA sequences including a single nucleotide polymorphism in which a base at position 101 is C or T in a polynucleotide represented by SEQ ID NO: 2.

Still another aspect of the present invention provides a composition for predicting a group at high risk of expression of blood ceramide including a preparation capable of detecting a single nucleotide polymorphism of a base at position 101 in a polynucleotide represented by SEQ ID NO: 1 or a single nucleotide polymorphism of a base at position 101 in a polynucleotide represented by SEQ ID NO: 2.

Still yet another aspect of the present invention provides a kit for predicting or diagnosing metabolic syndrome, including the composition for predicting or diagnosing the metabolic syndrome.

Still yet another aspect of the present invention provides a method for providing information for predicting or diagnosing metabolic syndrome including: (a) isolating DNA from a sample; and (b) confirming, in the isolated DNA, a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

Still yet another aspect of the present invention provides a kit for predicting a group at high risk of expression of blood ceramide, including the composition for predicting the group at high risk of expression of blood ceramide.

Still yet another aspect of the present invention provides a method for providing information for predicting a group at high risk of expression of blood ceramide including: (a) isolating DNA from a sample; and (b) confirming, in the isolated DNA, a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

Still yet another aspect of the present invention provides a method for diagnosing and treating metabolic syndrome including: (a) obtaining an analysis sample from a subject; (b) detecting, from the analysis sample of step (a), a polynucleotide consisting of 10 to 100 consecutive DNA sequences including a single nucleotide polymorphism in which a base at position 101 is C or G in a polynucleotide represented by SEQ ID NO: 1; or a polynucleotide consisting of 10 to 100 consecutive DNA sequences including a single nucleotide polymorphism in which a base at position 101 is C or T in a polynucleotide represented by SEQ ID NO: 2; (c) diagnosing metabolic syndrome in the case of the polynucleotide of step (b) in which a base at position 101 of the polynucleotide represented by SEQ ID NO: 1 is G or a base at position 101 of the polynucleotide represented by SEQ ID NO: 2 is T; and (d) administering an effective dose of metabolic syndrome therapeutic agent to a subject diagnosed as the metabolic syndrome in step (c).

Advantageous Effects

According to the embodiment of the present invention, it is possible to diagnose or predict metabolic syndrome by using the derived SNP marker, and to predict a group at high risk of expression of blood ceramide, thereby effectively diagnosing and managing patients with metabolic syndrome caused by a high expression of blood ceramide. On the basis of these effects, the present invention can find wide applications in the pharmaceutical industry, etc.

BRIEF DESCRIPTION OF THE DRAWINGS

FIG. 1 is a table showing P-values of blood ceramide levels and SNPs selected to be associated with metabolic syndrome.

DETAILED DESCRIPTION OF THE INVENTION

The present invention provides a marker composition for predicting or diagnosing metabolic syndrome including a polynucleotide consisting of 10 to 100 consecutive DNA sequences including a single nucleotide polymorphism in which a base at position 101 is C or G in a polynucleotide represented by SEQ ID NO: 1; or a polynucleotide consisting of 10 to 100 consecutive DNA sequences including a single nucleotide polymorphism in which a base at position 101 is C or T in a polynucleotide represented by SEQ ID NO: 2.

In the present invention, the term "single nucleotide polymorphism (SNP)" means that only a single base is different in a polymorphic site in which two or more alleles exist in one gene locus.

In the present invention, a polynucleotide represented by any one selected from the group consisting of SEQ ID NOs: 1 to 12 refers to a polymorphic sequence containing an SNP of a gene involved in metabolic syndrome, and is as described in Table 1 below. In the polynucleotide represented by any one selected from the group consisting of SEQ ID NOs: 1 to 12, an SNP position is a base at position 101.

TABLE 1

|  | NCBI refSNP ID | Nucleotide sequence (5'→3') |
|---|---|---|
| SEQ ID NO: 1 | rs75397325 | CAGGTACTTTTTTATGACCCAGATAT GATACCAGAAGACAGAGCACTACTGG ATGAGGGGGAGGTGGGTGCAAACTCT GCTATGGGAGCCCATGCCACTT[C/ G]AGTAAATAAATTAAGCTTTGTTCT CTCTTGAGGAATCTCATTCTTCCTGT TTATCCTTCTCTCTCACTGCTCCACA CTTCTCTGGAGTACTTGTTTCCAT |
| SEQ ID NO: 2 | rs12358192 | TTTAAAACCACCAGTTAGTCACATTT GATTTTTATCAGGCCTATAACGGTAC AAAACATTTCACTTCTGTTACTACAA AGCTGGAAGCTAATTTCAATTT[C/ T]CTACATCTCCACAAAAAAGCACCT ACAGACATGTCACTGCAAGATGCCCA GGCACCACAAAACCCCGGACCACTGC ATGGAGTCAGTGGGGAGCATACTG |
| SEQ ID NO: 3 | rs72759132 | AGTCCCTGTACAATTCAACATGGCAC TAGGTTTAGTCTGTTTATCTAGTCCA TAATAACTTTTAACTTAGAATAAACA TGTGACATTGCTAAAGAATAAG[A/ G]TAAGGCTTAAATTTTATTCATGGG CCCACTTACTGTGTCCTGAATATATT GCATAATTTCCTGCTTTGTGTCTTTG CTTTACTTGAAAATACTGCCTCAA |
| SEQ ID NO: 4 | rs4246316 | GCATCCCATAAATTCGTGTTGGGGAG GGCTTGGAAAGTCCAAGCTTCTTGTG TGGATGGCTTGGGGCCCAAGATAAAT GAACAGTTGCCACGATACACTC[C/ A/T]GTGCTCTGTGAGCGGAGGGAGC TCCCTTGGAGCCAGCCCAGCACCCTC CTCCCATGAGCACTCTGCCAGCTCCT GGCAGTGCTTCTGCTGTGGTGTGGAG |

TABLE 1-continued

| | NCBI refSNP ID | Nucleotide sequence (5'→3') |
|---|---|---|
| SEQ ID NO: 5 | rs80165332 | TTACTTTTTTATTTTTAAATTTCTAC TTTAACTAGGTAAATTATCATAAGAT GTAGAAAGAAAAGAAAGGTTAAGACT AATCCCCAACCATTATTTCCCA[T/ C]CTCTTCAATGTATCCAGTGTTAAC ACTCCACATATATGTTTCCATGGTAC CTTATCTTAGTTATAACACCCGTTTG ATCATATTGTCTGTATTGTCTGTT |
| SEQ ID NO: 6 | rs62106618 | TCGCACTCCAGCCTGGGCAACAGACT AAGACTTCACCTCAAAAAAAAAAAAA AAAGGTCACAAGAACATTTGCACCCA AAATTAAATGACTCAAGACCCC[G/ A]ACGTGCTGACATCAGACTTTGACT CCCCACAAAGTGTCTCCCTGATATGT CTGAGCCGCGACAAGTCTCTCATATG ACAAATACTTATATAATATGGGTG |
| SEQ ID NO: 7 | rs11006229 | TACTTACCTTTCAAATGATGGCTGTC TTCTTTCTCCTGATCAAAAATGAATG ACTAAATATGCCCACGGGCCCATTCA GGGATCGTACATGCTGTCGTCA[C/ T]GCTGCAAGAATAAGCAAAGCAACA TGCGTGTTATCACCAAGAATTTTTAC TCTTAATACTATTTCAGTTGAGAACG TGTTCTTAATATATGATAAGCCTC |
| SEQ ID NO: 8 | rs10826014 | TGCCATAGCCTCTGATCCAACAGGTT ATCAGTGATAACCCTGATCACCACTT AGCATACATGTATTTTCCTTATTCAT CTAGTTTGTCATCTTTCTCCCA[C/ T]TAGACTATTAGCTCCATAATACAC GTGTTGGTTGTTCTTTTTTTTTTCTA CTTGTCAATTTTGCTCACTGCCTAAA ATGTCTAAAGGAGGGCCTAGAAAA |
| SEQ ID NO: 9 | rs149162405 | ACTGGGCCACATGCTAACTCTATGTT TAACTGTTTCCTAAAGTGGCTGCATC ATTTTATAATCCCACCAGCAATGTAT CAGGATTCTAATTTCTCTATAT[C/ T]CTCATGAACACTTAATACCTGGTT TATTATTTTAGCAATCCTAGTGGTGT GAAATGGTATCTAACTGAGGTTTTGT TTTGTTTTGTTTTGTTGAGACAGA |
| SEQ ID NO: 10 | rs6109681 | TTTGCCTTCTTTCCCTCCTCCTTCTC TTCCTTTCCTCCTTAGTCTCCTTATT TCAATCTTGCCATGTCTATTAGAGAG ATGTTTGTTCTTCTGAATCTGC[C/ G/T]CTATATATATCTCTTGACTTTC CCTTTATATTTCTTTATCCTTTTCA CTGTCTTATGAAAAAAAATCATCAAT ATAATATTCTAGCTTATTAATTTGCC |
| SEQ ID NO: 11 | rs3906631 | GAACCTCTCTACGAACAAAAGACTAA ACCCAACCTGGTTACTTACTAAACAT GGAAGGAGGGGAATAAAAAGTTTTTA AGGAGAACGTGCATACATTAAT[A/ C]TTTCAATAAATTGTCCTATGATGT TTATAACAACAAAGCTTTATATATTT AAGAACATACAGATGCTTAGCATCCC TTGGGCTAAGAGCTGCCAAAATTT |
| SEQ ID NO: 12 | rs1813202 | GAGATGTTTGCTAAAGATTGGGCAAT AATTTAAATTTTTTATTAGCTTAAAA TGCAAATTAGAAAATGAACATAAATG TTGCACTCCTATGAGTTAATCA[A/ C/G/T]GACCATTACAGATCTATCAG CTGGTCAGAGATGATGTTCATTCTTC ATATTTGCTATCTTAAATTATTTACT ATCATATGTTTTTCAGTGTACAGATC TC |

In the present invention, the metabolic syndrome may represent at least three symptoms selected from the group consisting of central obesity, hyperglycemia, hypertriglyceridemia, hyperlipidemia and hypertension. The central obesity may be classified as central obesity when the waist circumference is 90 cm or more in men and 85 cm or more in women, and the hyperglycemia may be classified as hyperglycemia when a fasting blood sugar level is 100 mg/dL or more. The hyperlipidemia may be classified as hyperlipidemia when a blood HDL-cholesterol level is less than 40 mg/dL in men and less than 50 mg/dL in women, the hypertriglyceridemia may be classified as hypertriglyceridemia when the blood triglyceride level is 150 mg/dL or more, and the hypertension may be classified as hypertension when the systolic blood pressure is 130.85 mmHg or more and the diastolic blood pressure is 85 mmHg or more. In the present invention, the metabolic syndrome may be caused by a high expression of blood ceramide, and preferably, the ceramide may be any one selected from the group consisting of C16 dihydroceramide, C18 dihydroceramide, C24 dihydroceramide, C24:1 dihydroceramide, C16 ceramide, C18 ceramide and C20 ceramide.

In the present invention, the composition may further include at least one polynucleotide selected from the group consisting of a polynucleotide consisting of 10 to 100 consecutive DNA sequences including a single nucleotide polymorphism in which a base at position 101 is A or G in a polynucleotide represented by SEQ ID NO: 3; a polynucleotide consisting of 10 to 100 consecutive DNA sequences including a single nucleotide polymorphism in which a base at position 101 is C, A or T in a polynucleotide represented by SEQ ID NO: 4; a polynucleotide consisting of 10 to 100 consecutive DNA sequences including a single nucleotide polymorphism in which a base at position 101 is T or C in a polynucleotide represented by SEQ ID NO: 5; a polynucleotide consisting of 10 to 100 consecutive DNA sequences including a single nucleotide polymorphism in which a base at position 101 is G or A in a polynucleotide represented by SEQ ID NO: 6; a polynucleotide consisting of 10 to 100 consecutive DNA sequences including a single nucleotide polymorphism in which a base at position 101 is C or T in a polynucleotide represented by SEQ ID NO: 7; a polynucleotide consisting of 10 to 100 consecutive DNA sequences including a single nucleotide polymorphism in which a base at position 101 is C or T in a polynucleotide represented by SEQ ID NO: 8; a polynucleotide consisting of 10 to 100 consecutive DNA sequences including a single nucleotide polymorphism in which a base at position 101 is C or T in a polynucleotide represented by SEQ ID NO: 9; a polynucleotide consisting of 10 to 100 consecutive DNA sequences including a single nucleotide polymorphism in which a base at position 101 is C, G or T in a polynucleotide represented by SEQ ID NO: 10; a polynucleotide consisting of 10 to 100 consecutive DNA sequences including a single nucleotide polymorphism in which a base at position 101 is A or C in a polynucleotide represented by SEQ ID NO: 11; and a polynucleotide consisting of 10 to 100 consecutive DNA sequences including a single nucleotide polymorphism in which a base at position 101 is A, C, G or T in a polynucleotide represented by SEQ ID NO: 12. By the further included configuration, the marker composition of the present invention can be used to more accurately predict or diagnose metabolic syndrome, and confirm a type of ceramide, which is a risk factor for metabolic syndrome, more specifically and in detail.

In the present invention, the single nucleotide polymorphism in which the base at position 101 is C or G in the polynucleotide represented by SEQ ID NO: 1 may be highly correlated with metabolic syndrome, preferably highly correlated with metabolic syndrome caused by a high expression of blood ceramide, and more preferably highly correlated with metabolic syndrome caused by a high expression of blood C16 ceramide or blood C20 ceramide. In addition, when the base of the single nucleotide polymorphism site is G, it may be predicted or diagnosed as metabolic syndrome, and preferably predicted or diagnosed as metabolic syndrome caused by a high expression of blood C16 ceramide or blood C20 ceramide.

In the present invention, the single nucleotide polymorphism in which a base at position 101 is C or G in the polynucleotide represented by SEQ ID NO: 1 may be highly correlated with a high expression of metabolic syndrome, preferably highly correlated with a high expression of blood C16 ceramide or blood C20 ceramide. More preferably, when the base of the single nucleotide polymorphism site is G, it may be predicted as a group at high risk of expression of blood ceramide, and much more preferably predicted as a group at high risk of expression of blood C16 ceramide or blood C20 ceramide.

In the present invention, the single nucleotide polymorphism in which the base at position 101 is C or T in the polynucleotide represented by SEQ ID NO: 2 may be highly correlated with metabolic syndrome, preferably highly correlated with metabolic syndrome caused by a high expression of blood ceramide, and more preferably highly correlated with metabolic syndrome caused by a high expression of blood C16 ceramide, blood C18 ceramide or blood C20 ceramide. In addition, when the base of the single nucleotide polymorphism site is T, it may be predicted or diagnosed as metabolic syndrome, and preferably predicted or diagnosed as metabolic syndrome caused by a high expression of blood C16 ceramide, blood C18 ceramide or blood C20 ceramide.

In the present invention, the single nucleotide polymorphism in which the base at position 101 is C or T in the polynucleotide represented by SEQ ID NO: 2 may be highly correlated with a high expression of blood ceramide, and preferably highly correlated with a high expression of blood C16 ceramide, blood C18 ceramide or blood C20 ceramide. More preferably, when the base of the single nucleotide polymorphism site is T, it may be predicted as a group at high risk of expression of blood ceramide, and much more preferably predicted as a group at high risk of expression of blood C16 ceramide, blood C18 ceramide or blood C20 ceramide.

In the present invention, the single nucleotide polymorphism in which the base at position 101 is A or G in the polynucleotide represented by SEQ ID NO: 3 may be highly correlated with metabolic syndrome, preferably highly correlated with metabolic syndrome caused by a high expression of blood ceramide, and more preferably highly correlated with metabolic syndrome caused by a high expression of blood C16 ceramide. In addition, when the base of the single nucleotide polymorphism site is G, it may be predicted or diagnosed as metabolic syndrome, and preferably predicted or diagnosed as metabolic syndrome caused by a high expression of blood C16 ceramide.

In the present invention, the single nucleotide polymorphism in which the base at position 101 is A or G in the polynucleotide represented by SEQ ID NO: 3 may be highly correlated with a high expression of blood ceramide, and preferably highly correlated with a high expression of blood C16 ceramide. More preferably, when the base of the single nucleotide polymorphism site is G, it may be predicted as a group at high risk of expression of blood ceramide, and much more preferably predicted as a group at high risk of expression of blood C16 ceramide.

In the present invention, the single nucleotide polymorphism in which the base at position 101 is C, A or T in the polynucleotide represented by SEQ ID NO: 4 may be highly correlated with metabolic syndrome, preferably highly correlated with metabolic syndrome caused by a high expression of blood ceramide, and more preferably highly correlated with metabolic syndrome caused by a high expression of blood C16 ceramide. In addition, when the base of the single nucleotide polymorphism site is A or T, it may be predicted or diagnosed as metabolic syndrome, and preferably predicted or diagnosed as metabolic syndrome caused by a high expression of blood C16 ceramide.

In the present invention, the single nucleotide polymorphism in which the base at position 101 is C, A or T in the polynucleotide represented by SEQ ID NO: 4 may be highly correlated with a high expression of blood ceramide, and preferably highly correlated with a high expression of blood C16 ceramide. More preferably, when the base of the single nucleotide polymorphism site is A or T, it may be predicted as a group at high risk of expression of blood ceramide, and much more preferably predicted as a group at high risk of expression of blood C16 ceramide.

In the present invention, the single nucleotide polymorphism in which the base at position 101 is T or C in the polynucleotide represented by SEQ ID NO: 5 may be highly correlated with metabolic syndrome, preferably highly correlated with metabolic syndrome caused by a high expression of blood ceramide, and more preferably highly correlated with metabolic syndrome caused by a high expression of blood C16 ceramide. In addition, when the base of the single nucleotide polymorphism site is C, it may be predicted or diagnosed as metabolic syndrome, and preferably predicted or diagnosed as metabolic syndrome caused by a high expression of blood C16 ceramide.

In the present invention, the single nucleotide polymorphism in which the base at position 101 is T or C in the polynucleotide represented by SEQ ID NO: 5 may be highly correlated with a high expression of blood ceramide, and preferably highly correlated with a high expression of blood C16 ceramide. More preferably, when the base of the single nucleotide polymorphism site is C, it may be predicted as a group at high risk of expression of blood ceramide, and much more preferably predicted as a group at high risk of expression of blood C16 ceramide.

In the present invention, the single nucleotide polymorphism in which the base at position 101 is G or A in the polynucleotide represented by SEQ ID NO: 6 may be highly correlated with metabolic syndrome, preferably highly correlated with metabolic syndrome caused by a high expression of blood ceramide, and more preferably highly correlated with metabolic syndrome caused by a high expression of blood C18 dihydroceramide, blood C24 dihydroceramide or blood C24:1 dihydroceramide. In addition, when the base of the single nucleotide polymorphism site is A, it may be predicted or diagnosed as metabolic syndrome, and preferably predicted or diagnosed as metabolic syndrome caused by a high expression of blood C18 dihydroceramide, blood C24 dihydroceramide or blood C24:1 dihydroceramide.

In the present invention, the single nucleotide polymorphism in which the base at position 101 is G or A in the polynucleotide represented by SEQ ID NO: 6 may be highly correlated with a high expression of blood ceramide, and preferably highly correlated with a high expression of blood C18 dihydroceramide, blood C24 dihydroceramide or blood C24:1 dihydroceramide. More preferably, when the base of the single nucleotide polymorphism site is A, it may be predicted as a group at high risk of expression of blood ceramide, and much more preferably predicted as a group at high risk of expression of blood C18 dihydroceramide, blood C24 dihydroceramide or blood C24:1 dihydroceramide.

In the present invention, the single nucleotide polymorphism in which the base at position 101 is C or T in the polynucleotide represented by SEQ ID NO: 7 may be highly correlated with metabolic syndrome, preferably highly correlated with metabolic syndrome caused by a high expression of blood ceramide, and more preferably highly correlated with metabolic syndrome caused by a high expression of blood C24 dihydroceramide, blood C16 ceramide, blood C18 ceramide or blood C20 ceramide. In addition, when the base of the single nucleotide polymorphism site is T, it may be predicted or diagnosed as metabolic syndrome, and preferably predicted or diagnosed as metabolic syndrome caused by a high expression of blood C24 dihydroceramide, blood C16 ceramide, blood C18 ceramide or blood C20 ceramide.

In the present invention, the single nucleotide polymorphism in which the base at position 101 is C or T in the polynucleotide represented by SEQ ID NO: 7 may be highly correlated with a high expression of blood ceramide, and more preferably highly correlated with a high expression of blood C24 dihydroceramide, blood C16 ceramide, blood C18 ceramide or blood C20 ceramide. More preferably, when the base of the single nucleotide polymorphism site is T, it may be predicted as a group at high risk of expression of blood ceramide, and much more preferably predicted as a group at high risk of expression of blood C24 dihydroceramide, blood C16 ceramide, blood C18 ceramide or blood C20 ceramide.

In the present invention, the single nucleotide polymorphism in which the base at position 101 is C or T in the polynucleotide represented by SEQ ID NO: 8 may be highly correlated with metabolic syndrome, preferably highly correlated with metabolic syndrome caused by a high expression of blood ceramide, and more preferably highly correlated with metabolic syndrome caused by a high expression of blood C18 ceramide. In addition, when the base of the single nucleotide polymorphism site is T, it may be predicted or diagnosed as metabolic syndrome, and preferably predicted or diagnosed as metabolic syndrome caused by a high expression of blood C18 ceramide.

In the present invention, the single nucleotide polymorphism in which the base at position 101 is C or T in the polynucleotide represented by SEQ ID NO: 8 may be highly correlated with a high expression of blood ceramide, and preferably highly correlated with a high expression of blood C18 ceramide. More preferably, when the base of the single nucleotide polymorphism site is T, it may be predicted as a group at high risk of expression of blood ceramide, and much more preferably predicted as a group at high risk of expression of blood C18 ceramide.

In the present invention, the single nucleotide polymorphism in which the base at position 101 is C or T in the polynucleotide represented by SEQ ID NO: 9 may be highly correlated with metabolic syndrome, preferably highly correlated with metabolic syndrome caused by a high expression of blood ceramide, and more preferably highly correlated with metabolic syndrome caused by a high expression of blood C20 ceramide. In addition, when the base of the single nucleotide polymorphism site is T, it may be predicted or diagnosed as metabolic syndrome, and preferably predicted or diagnosed as metabolic syndrome caused by a high expression of blood C20 ceramide.

In the present invention, the single nucleotide polymorphism in which the base at position 101 is C or T in the polynucleotide represented by SEQ ID NO: 9 may be highly correlated with a high expression of blood ceramide, and preferably highly correlated with a high expression of blood C20 ceramide. More preferably, when the base of the single nucleotide polymorphism site is T, it may be predicted as a group at high risk of expression of blood ceramide, and much more preferably predicted as a group at high risk of expression of blood C20 ceramide.

In the present invention, the single nucleotide polymorphism in which the base at position 101 is C, G or T in the polynucleotide represented by SEQ ID NO: 10 may be highly correlated with metabolic syndrome, preferably highly correlated with metabolic syndrome caused by a high expression of blood ceramide, and more preferably highly correlated with metabolic syndrome caused by a high expression of blood C16 ceramide. In addition, when the base of the single nucleotide polymorphism site is G or T, it may be predicted or diagnosed as metabolic syndrome, and preferably predicted or diagnosed as metabolic syndrome caused by a high expression of blood C16 ceramide.

In the present invention, the single nucleotide polymorphism in which the base at position 101 is C, G or T in the polynucleotide represented by SEQ ID NO: 10 may be highly correlated with a high expression of blood ceramide, and preferably highly correlated with a high expression of blood C16 ceramide. More preferably, when the base of the single nucleotide polymorphism site is G or T, it may be predicted as a group at high risk of expression of blood ceramide, and much more preferably predicted as a group at high risk of expression of blood C16 ceramide.

In the present invention, the single nucleotide polymorphism in which the base at position 101 is A or C in the polynucleotide represented by SEQ ID NO: 11 may be highly correlated with metabolic syndrome, preferably highly correlated with metabolic syndrome caused by a high expression of blood ceramide, and more preferably highly correlated with metabolic syndrome caused by a high expression of blood C16 ceramide. In addition, when the base of the single nucleotide polymorphism site is C, it may be predicted or diagnosed as metabolic syndrome, and preferably predicted or diagnosed as metabolic syndrome caused by a high expression of blood C16 ceramide.

In the present invention, the single nucleotide polymorphism in which the base at position 101 is A or C in the polynucleotide represented by SEQ ID NO: 11 may be highly correlated with a high expression of blood ceramide, and preferably highly correlated with a high expression of blood C16 ceramide. More preferably, when the base of the single nucleotide polymorphism site is C, it may be predicted as a group at high risk of expression of blood ceramide, and much more preferably predicted as a group at high risk of expression of blood C16 ceramide.

In the present invention, the single nucleotide polymorphism in which the base at position 101 is A, C, G or T in the polynucleotide represented by SEQ ID NO: 12 may be highly correlated with metabolic syndrome, preferably highly correlated with metabolic syndrome caused by a high expression of blood ceramide, and more preferably highly correlated with metabolic syndrome caused by a high expression of blood C16 dihydroceramide or blood C16 ceramide. In addition, when the base of the single nucleotide polymorphism site is C, G or T, it may be predicted or diagnosed as metabolic syndrome, and preferably predicted or diagnosed as metabolic syndrome caused by a high expression of blood C16 dihydroceramide or blood C16 ceramide.

In the present invention, the single nucleotide polymorphism in which the base at position 101 is A, C, G or T in the polynucleotide represented by SEQ ID NO: 12 may be highly correlated with a high expression of blood ceramide, and preferably highly correlated with a high expression of blood C16 dihydroceramide or blood C16 ceramide. More preferably, when the base of the single nucleotide polymorphism site is C, G or T, it may be predicted as a group at high risk of expression of blood ceramide, and much more preferably predicted as a group at high risk of expression of blood C16 dihydroceramide or blood C16 ceramide.

In addition, the present invention provides a composition for predicting or diagnosing metabolic syndrome including a preparation capable of detecting a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

In the present invention, the composition may further include a preparation capable of detecting at least one single nucleotide polymorphism selected from the group consisting of a single nucleotide polymorphism in which a base at position 101 is A or G in a polynucleotide represented by SEQ ID NO: 3; a single nucleotide polymorphism in which a base at position 101 is C, A or T in a polynucleotide represented by SEQ ID NO: 4; a single nucleotide polymorphism in which a base at position 101 is T or C in a polynucleotide represented by SEQ ID NO: 5; a single nucleotide polymorphism in which a base at position 101 is G or A in a polynucleotide represented by SEQ ID NO: 6; a single nucleotide polymorphism in which a base at position 101 is C or T in a polynucleotide represented by SEQ ID NO: 7; a single nucleotide polymorphism in which a base at position 101 is C or T in a polynucleotide represented by SEQ ID NO: 8; a single nucleotide polymorphism in which a base at position 101 is C or T in a polynucleotide represented by SEQ ID NO: 9; a single nucleotide polymorphism in which a base at position 101 is C, G or T in a polynucleotide represented by SEQ ID NO: 10; a single nucleotide polymorphism in which a base at position 101 is A or C in a polynucleotide represented by SEQ ID NO: 11; and a single nucleotide polymorphism in which a base at position 101 is A, C, G or T in a polynucleotide represented by SEQ ID NO: 12.

In the present invention, the detectable preparation may be a primer pair or a probe capable of amplifying or detecting the polynucleotide including the single nucleotide polymorphism site.

In the present invention, the term "primer" refers to a nucleotide sequence having a short free 3' hydroxyl group, and a short sequence capable of forming a base pair with a complementary template and serving as a starting point for copying a template strand. The appropriate length of the primer may vary depending on a purpose of use, but generally consists of 15 to 30 bases. A primer sequence need not be perfectly complementary to a template, but should be sufficiently complementary to hybridize with the template.

In the present invention, the term "probe" is a hybridization probe and refers to an oligonucleotide capable of sequence-specifically binding to a complementary strand of a nucleic acid. The probe of the present invention is an allele-specific probe, and has a polymorphism site in a nucleic acid fragment derived from two individuals in the same species, and hybridizes with a DNA fragment derived from one individual, but does not hybridize with a fragment derived from the other individual. In this case, the hybridization conditions show a significant difference in hybridization strength between alleles, and need to be sufficiently stringent to hybridize with only one of the alleles. Preferably, the probe may be a single strand, more preferably deoxyribonucleotide for maximum efficiency in hybridization, but is not limited thereto. As the probe, a sequence perfectly complementary to the sequence including the SNP may be used, but a substantially complementary sequence may also be used within a range that does not interfere with specific hybridization.

In the present invention, the composition may further include one or more other component compositions, solutions or devices suitable for the analyzing method.

In addition, the present invention provides a marker composition for predicting a group at high risk of expression of blood ceramide including a polynucleotide consisting of 10 to 100 consecutive DNA sequences including a single nucleotide polymorphism in which a base at position 101 is C or G in a polynucleotide represented by SEQ ID NO: 1 or a polynucleotide consisting of 10 to 100 consecutive DNA sequences including a single nucleotide polymorphism in which a base at position 101 is C or T in a polynucleotide represented by SEQ ID NO: 2.

In the present invention, the ceramide may be any one selected from the group consisting of C16 dihydroceramide, C18 dihydroceramide, C24 dihydroceramide, C24:1 dihydroceramide, C16 ceramide, C18 ceramide and C20 ceramide.

In the present invention, the composition may further include at least one polynucleotide selected from the group consisting of a polynucleotide consisting of 10 to 100 consecutive DNA sequences including a single nucleotide polymorphism in which a base at position 101 is A or G in a polynucleotide represented by SEQ ID NO: 3; a polynucleotide consisting of 10 to 100 consecutive DNA sequences including a single nucleotide polymorphism in which a base at position 101 is C, A or T in a polynucleotide represented by SEQ ID NO: 4; a polynucleotide consisting of 10 to 100 consecutive DNA sequences including a single nucleotide polymorphism in which a base at position 101 is T or C in a polynucleotide represented by SEQ ID NO: 5; a polynucleotide consisting of 10 to 100 consecutive DNA sequences including a single nucleotide polymorphism in which a base at position 101 is G or A in a polynucleotide represented by SEQ ID NO: 6; a polynucleotide consisting of 10 to 100 consecutive DNA sequences including a single nucleotide polymorphism in which a base at position 101 is C or T in a polynucleotide represented by SEQ ID NO: 7; a polynucleotide consisting of 10 to 100 consecutive DNA sequences including a single nucleotide polymorphism in which a base at position 101 is C or T in a polynucleotide represented by SEQ ID NO: 8; a polynucleotide consisting of 10 to 100 consecutive DNA sequences including a single nucleotide polymorphism in which a base at position 101 is C or T in a polynucleotide represented by SEQ ID NO: 9; a polynucleotide consisting of 10 to 100 consecutive DNA sequences including a single nucleotide polymorphism in which a base at position 101 is C, G or T in a polynucleotide represented by SEQ ID NO: 10; a polynucleotide consisting of 10 to 100 consecutive DNA sequences including a single nucleotide polymorphism in which a base at position 101 is A or C in a polynucleotide represented by SEQ ID NO: 11; and a polynucleotide consisting of 10 to 100 consecutive DNA sequences including a single nucleotide polymorphism in which a base at position 101 is A, C, G or T in a polynucleotide represented by SEQ ID NO: 12.

In addition, the present invention provides a composition for predicting a group at high risk of expression of blood ceramide including a preparation capable of detecting a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

In the present invention, the ceramide may be any one selected from the group consisting of C16 dihydroceramide, C18 dihydroceramide, C24 dihydroceramide, C24:1 dihydroceramide, C16 ceramide, C18 ceramide and C20 ceramide.

In the present invention, the composition may further include a preparation capable of detecting at least one single nucleotide polymorphism selected from the group consisting of a single nucleotide polymorphism in which a base at position 101 is A or G in a polynucleotide represented by SEQ ID NO: 3; a single nucleotide polymorphism in which a base at position 101 is C, A or T in a polynucleotide represented by SEQ ID NO: 4; a single nucleotide polymorphism in which a base at position 101 is T or C in a polynucleotide represented by SEQ ID NO: 5; a single nucleotide polymorphism in which a base at position 101 is G or A in a polynucleotide represented by SEQ ID NO: 6; a single nucleotide polymorphism in which a base at position 101 is C or T in a polynucleotide represented by SEQ ID NO: 7; a single nucleotide polymorphism in which a base at position 101 is C or T in a polynucleotide represented by SEQ ID NO: 8; a single nucleotide polymorphism in which a base at position 101 is C or T in a polynucleotide represented by SEQ ID NO: 9; a single nucleotide polymorphism in which a base at position 101 is C, G or T in a polynucleotide represented by SEQ ID NO: 10; a single nucleotide polymorphism in which a base at position 101 is A or C in a polynucleotide represented by SEQ ID NO: 11; and a single nucleotide polymorphism in which a base at position 101 is A, C, G or T in a polynucleotide represented by SEQ ID NO: 12.

In addition, the present invention provides a kit for predicting or diagnosing metabolic syndrome, including the composition for predicting or diagnosing the metabolic syndrome.

Further, the present invention provides a kit for predicting a group at high risk of expression of blood ceramide, including the composition for predicting the group at high risk of expression of blood ceramide.

In the present invention, the kit may be at least one selected from the group consisting of a polymerase chain reaction (PCR) kit; a ligase chain reaction (LCR) kit; a Gap-LCR, a repair chain reaction kit, a transcription-mediated amplification (TMA) kit, a self sustained sequence replication kit, a selective amplification kit of target polynucleotide sequences, a consensus sequence priming polymerase chain reaction (CP-PCR) kit, an arbitrary priming polymerase chain reaction (AP-PCR) kit, a nucleic acid sequence-based amplification (NASBA) kit, a strand displacement amplification kit, a loop-mediated isothermal amplification (LAMP) kit, a multiplex PCR kit, a nested-PCR kit, a single tube nested-PCR kit, a reverse transcription-polymerase chain reaction (RT-PCR) kit, an inverse polymerase chain reaction (inverse PCR) kit, a real-time polymerase chain reaction (RT-PCR) kit, and a real-time quantitative polymerase chain reaction (RQ-PCR) kit, but the present invention is not limited thereto.

In addition, the present invention provides a method for providing information for predicting or diagnosing metabolic syndrome including (a) isolating DNA from a sample; and (b) confirming, in the isolated DNA, a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

In the present invention, step (b) may further include confirming, in the isolated DNA, at least one single nucleotide polymorphism selected from the group consisting of a single nucleotide polymorphism in which a base at position 101 is A or G in a polynucleotide represented by SEQ ID NO: 3; a single nucleotide polymorphism in which a base at position 101 is C, A or T in a polynucleotide represented by SEQ ID NO: 4; a single nucleotide polymorphism in which a base at position 101 is T or C in a polynucleotide represented by SEQ ID NO: 5; a single nucleotide polymorphism in which a base at position 101 is G or A in a polynucleotide represented by SEQ ID NO: 6; a single nucleotide polymorphism in which a base at position 101 is C or T in a polynucleotide represented by SEQ ID NO: 7; a single nucleotide polymorphism in which a base at position 101 is C or T in a polynucleotide represented by SEQ ID NO: 8; a single nucleotide polymorphism in which a base at position 101 is C or T in a polynucleotide represented by SEQ ID NO: 9; a single nucleotide polymorphism in which a base at position 101 is C, G or T in a polynucleotide represented by SEQ ID NO: 10; a single nucleotide polymorphism in which a base at position 101 is A or C in a polynucleotide represented by SEQ ID NO: 11; and a single nucleotide polymorphism in which a base at position 101 is A, C, G or T in a polynucleotide represented by SEQ ID NO: 12. By the further included configuration, it is possible to provide information for more accurately predicting or diagnosing metabolic syndrome, and more specific and detailed information about the type of ceramide, which is a risk factor for metabolic syndrome, may be provided.

In the present invention, the sample in step (a) may include, without limitation, biological samples from a subject to be diagnosed, from which a nucleic acid, particularly DNA, required for detecting a single nucleotide polymorphism site can be extracted, and may include, for example, samples such as tissue, cells, whole blood, serum, plasma, saliva, sputum, cerebrospinal fluid or urine, but is not limited thereto.

In the present invention, the confirming of the single nucleotide polymorphism means confirming a genotype of a single nucleotide polymorphism site in the isolated DNA, and specifically, may be confirming the genotype by analyzing the isolated DNA through methods such as sequencing analysis using an automated sequencing analyzer, pyrosequencing, hybridization by microarray, PRC-restriction fragment length polymorphism (RELP), PCR-single strand conformation polymorphism (SSCP), PCR-specific sequence oligonucleotide (SSO), allele specific oligonucleotide (ASO) hybridization combined with PCR-SSO and dot hybridization, TaqMan-PCR, MALDI-TOF/MS, rolling circle amplification (RCA), high resolution melting (HRM), primer extension, Southern blot hybridization, dot hybridization, etc.

In addition, the present invention provides a method for providing information for predicting a group at high risk of expression of blood ceramide including (a) isolating DNA from a sample; and (b) confirming, in the isolated DNA, a single nucleotide polymorphism of a base at position 101 in a polynucleotide consisting of SEQ ID NO: 1 or a single nucleotide polymorphism of a base at position 101 in a polynucleotide consisting of SEQ ID NO: 2.

In the present invention, step (b) may further include confirming, in the isolated DNA, at least one single nucleotide polymorphism selected from the group consisting of a single nucleotide polymorphism in which a base at position 101 is A or G in a polynucleotide represented by SEQ ID NO: 3; a single nucleotide polymorphism in which a base at position 101 is C, A or T in a polynucleotide represented by SEQ ID NO: 4; a single nucleotide polymorphism in which a base at position 101 is T or C in a polynucleotide represented by SEQ ID NO: 5; a single nucleotide polymorphism in which a base at position 101 is G or A in a polynucleotide represented by SEQ ID NO: 6; a single nucleotide polymorphism in which a base at position 101 is C or T in a polynucleotide represented by SEQ ID NO: 7; a single nucleotide polymorphism in which a base at position 101 is C or T in a polynucleotide represented by SEQ ID NO: 8; a single nucleotide polymorphism in which a base at position 101 is C or T in a polynucleotide represented by SEQ ID NO: 9; a single nucleotide polymorphism in which a base at position 101 is C, G or T in a polynucleotide represented by SEQ ID NO: 10; a single nucleotide polymorphism in which a base at position 101 is A or C in a polynucleotide represented by SEQ ID NO: 11; and a single nucleotide polymorphism in which a base at position 101 is A, C, G or T in a polynucleotide represented by SEQ ID NO: 12. More specific and detailed information about the type of high risk of expression of blood ceramide and the like can be provided by the further included configuration.

The present invention provides a method for diagnosing and/or treating metabolic syndrome using an SNP associated with the metabolic syndrome and a blood ceramide concentration. The method for diagnosing and/or treating metabolic syndrome according to the present invention includes (a) obtaining an analysis sample from a subject; (b) detecting, from the analysis sample of step (a), a polynucleotide consisting of 10 to 100 consecutive DNA sequences including a single nucleotide polymorphism in which a base at position 101 is C or G in a polynucleotide represented by SEQ ID NO: 1; or a polynucleotide consisting of 10 to 100 consecutive DNA sequences including a single nucleotide polymorphism in which a base at position 101 is C or T in a polynucleotide represented by SEQ ID NO: 2; (c) diagnosing metabolic syndrome in the case of the polynucleotide of step (b) in which a base at position 101 of the polynucleotide represented by SEQ ID NO: 1 is G or a base at position 101 of the polynucleotide represented by SEQ ID NO: 2 is T; and (d) administering an effective dose of metabolic syndrome therapeutic agent to a subject diagnosed as the metabolic syndrome in step (c).

In the present invention, step (b) preferably further includes detecting, from the analysis sample of step (a), at least one polynucleotide selected from the group consisting of a polynucleotide consisting of 10 to 100 consecutive DNA sequences including a single nucleotide polymorphism in which a base at position 101 is A or G in a polynucleotide represented by SEQ ID NO: 3; a polynucleotide consisting of 10 to 100 consecutive DNA sequences including a single nucleotide polymorphism in which a base at position 101 is C, A or T in a polynucleotide represented by SEQ ID NO: 4; a polynucleotide consisting of 10 to 100 consecutive DNA sequences including a single nucleotide polymorphism in which a base at position 101 is T or C in a polynucleotide represented by SEQ ID NO: 5; a polynucleotide consisting of 10 to 100 consecutive DNA sequences including a single nucleotide polymorphism in which a base at position 101 is G or A in a polynucleotide represented by SEQ ID NO: 6; a polynucleotide consisting of 10 to 100 consecutive DNA sequences including a single nucleotide polymorphism in which a base at position 101 is C or T in a polynucleotide represented by SEQ ID NO: 7; a polynucleotide consisting of 10 to 100 consecutive DNA sequences including a single nucleotide polymorphism in which a base at position 101 is C or T in a polynucleotide represented by SEQ ID NO: 8; a polynucleotide consisting of 10 to 100 consecutive DNA sequences including a single nucleotide polymorphism in which a base at position 101 is C or T in a polynucleotide represented by SEQ ID NO: 9; a polynucleotide consisting of 10 to 100 consecutive DNA sequences including a single nucleotide polymorphism in which a base at position 101 is C, G or T in a polynucleotide represented by SEQ ID NO: 10; a polynucleotide consisting of 10 to 100 consecutive DNA sequences including a single nucleotide polymorphism in which a base at position 101 is A or C in a polynucleotide represented by SEQ ID NO: 11; and a polynucleotide consisting of 10 to 100 consecutive DNA sequences including a single nucleotide polymorphism in which a base at position 101 is A, C, G or T in a polynucleotide represented by SEQ ID NO: 12.

In the present invention, the metabolic syndrome therapeutic agent may be at least one selected from the group consisting of pitavastatin, amlodipine besylate, losartan, carvedilol, lovastatin, pravastatin, simvastatin, fluvastatin, atorvastatin, rosuvastatin, fenofibrate, gemfibrozil, bezafibrate, pravafenix, ezetimibe, niacin, probucol, orlistat, lorcaserin, diethylpropion, phentermine, mazindol, phendimetrazine, lorcaserin, liraglutide, nicotinic acid and acipimox, but is not limited thereto.

In the present invention, the subject diagnosed with the metabolic syndrome is preferably a group at high risk of blood ceramide.

Duplicated contents are omitted in consideration of the complexity of the present specification, and terms not defined otherwise in the present specification have the meanings commonly used in the art to which the present invention pertains.

Hereinafter, the present invention will be described in detail by Examples. However, the following Examples are just illustrative of the present invention, and the contents of the present invention are not limited to the following Examples.

MODES FOR THE INVENTION

Example 1. Experimental Method 1.1 Recruitment of Experimental Participants

Participants in metabolic syndrome, who agreed to blood collection, were recruited by Hanaro Medical Center (Korea) according to the guidelines. A collection protocol received ethical approval from the Seoul clinical research institute and was in line with the principle of the Helsinki Declaration. All participants were provided with information about a blood test and an SNP genotype test using a blood sample.

1.2 Selection of Metabolic Syndrome Participants

Participants in health checkups included men and women over 18 years of age. If three or more of central obesity, hyperglycemia, hypertriglyceridemia, hyperlipidemia and hypertension are satisfied, the participants were clinically diagnosed with metabolic syndrome. The diagnostic criteria were based on five standards of metabolic syndrome, defined based on the prevention and treatment guidelines of metabolic syndrome of Korean adults published by the Korean Society of Home Medical Medicine. When the waist circumference was 90 cm or more in men and 85 cm or more in women, the metabolic syndrome was classified as the central obesity. If a fasting blood sugar level was 100 mg/dL or more, the metabolic syndrome was classified as hyperglycemia. When the blood HDL-cholesterol level was less than 40 mg/dL in men and less than 50 mg/dL in women, the metabolic syndrome was classified as hyperlipidemia. When a blood triglyceride level is 150 mg/dL or higher, the metabolic syndrome was classified as hypertriglyceridemia. When the systolic blood pressure was 130.85 mmHg or more and the diastolic blood pressure was 85 mmHg or more, the metabolic syndrome was classified as hypertension.

1.3 Genome Wide SNP Genotyping

DNA samples were obtained from 200 IA of the whole blood using a MagNA Pure 96 DNA and Viral NA SV kit (Roche Life Science, USA) and a MagNA Pure 96 system (Roche Life Science, USA). 200 IA of a DNA sample was subjected to genotyping for 827,783 SNPs using a GeneTitan™ Multi-Channel instrument and a KNIH biobank array v1.1 chip according to the manufacturer's instructions. A CEL file as the genotyping result was converted into a PLINK input format file (ped format) using the Axiom Analysis Suite program. Samples that did not reach DQC≥0.82 and call rate≥0.97 as cutoff criteria were subjected to genotyping again using a KNIH Bio Bank Array v1.1 chip. Genotyped ped files were analyzed using PLINK (version 1.90). SNPs classified as mendel multigen were treated as missing, and SNPs with low genotyping rates of less than 0.05, low minor allele frequencies of less than 0.01, and outlying heterozygosity of less than 0.31 or greater than 0.33 were excluded. Hardy-Weinberg Equilibrium analysis was performed on the selected SNPs, and when the p-value exceeded 0.05, the selected SNPs were excluded from further analysis.

1.4 Calculation of SNP Association

For gene symbol annotating, SNPs with significant association were analyzed using an Ensembl API client (version 1.1.5 including Genome hg19). The SNPs included in a ceramide pathway gene, and having a p-value of less than 0.05 as a result of Hardy-Weinberg equilibrium analysis were derived. For the selected SNPs, the associations with blood dihydroceramides and ceramide levels were analyzed using a linear regression modeling approach. Association analysis was performed for each property of dihydroceramide and ceramide using R package software (version 3.5.3).

1.5 Pathway Analysis of Selected SNPs

In order to perform pathway analysis to search for functional terms, genes were annotated using a Python program for selected SNPs with P values of less than 0.05. For pathway analysis, an NDEx integrated query (version 1.0) website was used, and an integrated genetic database of Harmonizome online version was used for gene functional term analysis. A pathway with P-values of less than 0.05 was considered a significant pathway.

Example 2. Derivation of SNP Markers Related to Increased Blood Ceramide Concentration in Patients with Metabolic Syndrome Through the analysis of Example 1.3, SNPs showing a specifically high frequency were selected in a metabolic syndrome patient group compared to a normal control group. For the selected SNPs, genes were annotated as in Example 1.4 to derive SNPs belonging to the ceramide pathway gene, and association between the derived SNPs and the levels of blood dihydroceramides and ceramides was analyzed, and P-values of the SNPs and the levels of blood dihydroceramides and ceramides were illustrated in FIG. 1.

As illustrated in FIG. 1, it was confirmed that 12 SNPs (rs75397325, rs72759132, rs4246316, rs80165332, rs62106618, rs12358192, rs11006229, rs10826014, rs149162405, rs6109681, rs3906631, rs1813202) were significantly associated with the levels of blood dihydroceramides and ceramides. Particularly, rs75397325 was closely associated with a blood C16_ceramide concentration and a blood C20_ceramide concentration, and rs12358192 was closely associated with a blood C16_ceramide concentration, a blood C18_ceramide concentration and a blood C20_ceramide concentration.

The 12 SNPs showed a particularly high frequency in patients with metabolic syndrome compared to a normal control, and the nucleotide sequences of the SNPs of a subject were confirmed to predict or diagnose metabolic syndrome, and a significant association with the levels of blood dihydroceramide or ceramide was confirmed to be used to predict a group at high risk of expression of blood ceramide. Furthermore, the high expression of blood ceramide corresponds to one of major causes of metabolic syndrome, and thus, can be used for predicting or diagnosing metabolic syndrome due to the high expression of ceramide.

As described above, specific parts of the present invention have been described in detail, and it will be apparent to those skilled in the art that these specific techniques are merely preferred embodiments, and the scope of the present invention is not limited thereto. Therefore, the substantial scope of the present invention will be defined by the appended claims and their equivalents.

What is claimed is:

1. A method for diagnosing and treating metabolic syndrome in a subject, comprising:

(a) obtaining a sample comprising nucleic acids from a subject;

(b) assaying the sample to detect the presence of G allele at SNP rs75397325;

(c) diagnosing the subject as having metabolic syndrome based on the detection of the G allele at SNP rs75397325; and (d) administering an effective dose of a metabolic syndrome therapeutic agent to the subject diagnosed as having the metabolic syndrome in step (c), wherein the metabolic syndrome therapeutic agent is at least one selected from the group consisting of pitavastatin, amlodipine besylate, losartan, carvedilol, lovastatin, pravastatin, simvastatin, fluvastatin, atorvastatin, rosuvastatin, fenofibrate, gemfibrozil, bezafibrate, pravafenix, ezetimibe, niacin, probucol, orlistat, lorcaserin, diethylpropion, phentermine, mazindol, phendimetrazine, lorcaserin, liraglutide, nicotinic acid and acipimox.

2. The method for diagnosing and treating the metabolic syndrome of claim 1, wherein step (b) further includes detecting, from the analysis sample of step (a), at least one polynucleotide selected from the group consisting of a polynucleotide consisting of 10 to 100 consecutive DNA sequences including a single nucleotide polymorphism in which a base at position 101 is A or G in a polynucleotide represented by SEQ ID NO: 3;

a polynucleotide consisting of 10 to 100 consecutive DNA sequences including a single nucleotide polymorphism in which a base at position 101 is C, A or T in a polynucleotide represented by SEQ ID NO: 4;

a polynucleotide consisting of 10 to 100 consecutive DNA sequences including a single nucleotide polymorphism in which a base at position 101 is T or C in a polynucleotide represented by SEQ ID NO: 5;

a polynucleotide consisting of 10 to 100 consecutive DNA sequences including a single nucleotide polymorphism in which a base at position 101 is G or A in a polynucleotide represented by SEQ ID NO: 6;

a polynucleotide consisting of 10 to 100 consecutive DNA sequences including a single nucleotide polymorphism in which a base at position 101 is C or T in a polynucleotide represented by SEQ ID NO: 7;

a polynucleotide consisting of 10 to 100 consecutive DNA sequences including a single nucleotide polymorphism in which a base at position 101 is C or T in a polynucleotide represented by SEQ ID NO: 8;

a polynucleotide consisting of 10 to 100 consecutive DNA sequences including a single nucleotide polymorphism in which a base at position 101 is C or T in a polynucleotide represented by SEQ ID NO: 9;

a polynucleotide consisting of 10 to 100 consecutive DNA sequences including a single nucleotide polymorphism in which a base at position 101 is C, G or T in a polynucleotide represented by SEQ ID NO: 10;

a polynucleotide consisting of 10 to 100 consecutive DNA sequences including a single nucleotide polymorphism in which a base at position 101 is A or C in a polynucleotide represented by SEQ ID NO: 11; and a polynucleotide consisting of 10 to 100 consecutive DNA sequences including a single nucleotide polymorphism in which a base at position 101 is A, C, G or T in a polynucleotide represented by SEQ ID NO: 12.

3. The method for diagnosing and treating the metabolic syndrome of claim 2, wherein the subject diagnosed with the metabolic syndrome is a subject at high risk of increased levels of blood ceramide.

4. The method for diagnosing and treating the metabolic syndrome of claim 1, wherein the subject diagnosed with the metabolic syndrome is a subject at high risk of increased levels of blood ceramide, and wherein the ceramide is any one selected from the group consisting of C16 dihydroceramide, C18 dihydroceramide, C24 dihydroceramide, C24:1 dihydroceramide, C16 ceramide, C18 ceramide and C20 ceramide.

5. The method for diagnosing and treating the metabolic syndrome of claim 1, wherein the metabolic syndrome is characterized by at least three symptoms selected from the group consisting of central obesity, hyperglycemia, hypertriglyceridemia, hyperlipidemia and hypertension.

* * * * *

SEQUENCE LISTING

<160> NUMBER OF SEQ ID NOS: 12

<210> SEQ ID NO 1
<211> LENGTH: 201
<212> TYPE: DNA
<213> ORGANISM: Homo sapiens

<400> SEQUENCE: 1
caggtacttt tttatgaccc agatatgata ccagaagaca gagcactact ggatgagggg      60
gaggtgggtg caaactctgc tatgggagcc catgccactt sagtaaataa attaagcttt     120
gttctctctt gaggaatctc attcttcctg tttatccttc tctctcactg ctccacactt     180

```
ctctggagta cttgtttcca t                                                  201

<210> SEQ ID NO 2
<211> LENGTH: 201
<212> TYPE: DNA
<213> ORGANISM: Homo sapiens

<400> SEQUENCE: 2
tttaaaacca ccagttagtc acatttgatt tttatcaggc ctataacggt acaaaacatt     60
tcacttctgt tactacaaag ctggaagcta atttcaattt yctacatctc cacaaaaaag    120
cacctacaga catgtcactg caagatgccc aggcaccaca aaaccccgga ccactgcatg    180
gagtcagtgg ggagcatact g                                               201

<210> SEQ ID NO 3
<211> LENGTH: 201
<212> TYPE: DNA
<213> ORGANISM: Homo sapiens

<400> SEQUENCE: 3
agtccctgta caattcaaca tggcactagg tttagtctgt ttatctagtc cataataact     60
tttaacttag aataaacatg tgacattgct aaagaataag rtaaggctta aattttattc    120
atgggcccac ttactgtgtc ctgaatatat tgcataattt cctgctttgt gtctttgctt    180
tacttgaaaa tactgcctca a                                               201

<210> SEQ ID NO 4
<211> LENGTH: 201
<212> TYPE: DNA
<213> ORGANISM: Homo sapiens

<400> SEQUENCE: 4
gcatcccata aattcgtgtt ggggagggct tggaaagtcc aagcttcttg tgtggatggc     60
ttggggccca agataaatga acagttgcca cgatacactc hgtgctctgt gagcggaggg    120
agctcccttg gagccagccc agcaccctcc tcccatgagc actctgccag ctcctggcag    180
tgcttctgct gtggtgtgga g                                               201

<210> SEQ ID NO 5
<211> LENGTH: 201
<212> TYPE: DNA
<213> ORGANISM: Homo sapiens

<400> SEQUENCE: 5
ttactttttt atttttaaat ttctacttta actaggtaaa ttatcataag atgtagaaag     60
aaaagaaagg ttaagactaa tccccaacca ttatttccca yctcttcaat gtatccagtg    120
ttaacactcc acatatatgt ttccatggta ccttatctta gttataacac ccgtttgatc    180
atattgtctg tattgtctgt t                                               201

<210> SEQ ID NO 6
<211> LENGTH: 201
<212> TYPE: DNA
<213> ORGANISM: Homo sapiens

<400> SEQUENCE: 6
tcgcactcca gcctgggcaa cagactaaga cttcacctca aaaaaaaaaa aaaaaggtca     60
caagaacatt tgcacccaaa attaaatgac tcaagacccc racgtgctga catcagactt    120
```

-continued

```
tgactcccca caaagtgtct ccctgatatg tctgagccgc gacaagtctc tcatatgaca        180
aatacttata taatatgggt g                                                    201

<210> SEQ ID NO 7
<211> LENGTH: 201
<212> TYPE: DNA
<213> ORGANISM: Homo sapiens

<400> SEQUENCE: 7
tacttacctt tcaaatgatg gctgtcttct ttctcctgat caaaaatgaa tgactaaata        60
tgcccacggg cccattcagg gatcgtacat gctgtcgtca ygctgcaaga ataagcaaag       120
caacatgcgt gttatcacca agaatttttta ctcttaatac tatttcagtt gagaacgtgt       180
tcttaatata tgataagcct c                                                    201

<210> SEQ ID NO 8
<211> LENGTH: 201
<212> TYPE: DNA
<213> ORGANISM: Homo sapiens

<400> SEQUENCE: 8
tgccatagcc tctgatccaa caggttatca gtgataaccc tgatcaccac ttagcataca        60
tgtattttcc ttattcatct agtttgtcat ctttctccca ytagactatt agctccataa       120
tacacgtgtt ggttgttctt tttttttttct acttgtcaat tttgctcact gcctaaaatg       180
tctaaaggag ggcctagaaa a                                                    201

<210> SEQ ID NO 9
<211> LENGTH: 201
<212> TYPE: DNA
<213> ORGANISM: Homo sapiens

<400> SEQUENCE: 9
actgggccac atgctaactc tatgtttaac tgtttcctaa agtggctgca tcattttata        60
atcccaccag caatgtatca ggattctaat ttctctatat yctcatgaac acttaatacc       120
tggtttatta ttttagcaat cctagtggtg tgaaatggta tctaactgag gttttgtttt       180
gttttgtttt gttgagacag a                                                    201

<210> SEQ ID NO 10
<211> LENGTH: 201
<212> TYPE: DNA
<213> ORGANISM: Homo sapiens

<400> SEQUENCE: 10
tttgccttct ttccctcctc cttctcttcc tttcctcctt agtctcctta tttcaatctt        60
gccatgtcta ttagagagat gtttgttctt ctgaatctgc bctatatata tctcttgact       120
ttccctttat atttctttta tccttttcac tgtcttatga aaaaaaatca tcaatataat       180
attctagctt attaatttgc c                                                    201

<210> SEQ ID NO 11
<211> LENGTH: 201
<212> TYPE: DNA
<213> ORGANISM: Homo sapiens

<400> SEQUENCE: 11
gaacctctct acgaacaaaa gactaaaccc aacctggtta cttactaaac atggaaggag        60
gggaataaaa agtttttaag gagaacgtgc atacattaat mtttcaataa attgtcctat       120
```

-continued

```
gatgtttata acaacaaagc tttatatatt taagaacata cagatgctta gcatcccttg      180
ggctaagagc tgccaaaatt t                                                201

<210> SEQ ID NO 12
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t

<400> SEQUENCE: 12
gagatgtttg ctaaagattg ggcaataatt taaatttttt attagcttaa aatgcaaatt       60
agaaaatgaa cataaatgtt gcactcctat gagttaatca ngaccattac agatctatca      120
gctggtcaga gatgatgttc attcttcata tttgctatct taaattattt actatcatat      180
gtttttcagt gtacagatct c                                                201
```